United States Patent
Kim et al.

(10) Patent No.: US 11,052,380 B2
(45) Date of Patent: *Jul. 6, 2021

(54) AGGLOMERATED ODH CATALYST

(71) Applicant: NOVA Chemicals (International) S.A., Fribourg (CH)

(72) Inventors: Yoonhee Kim, Calgary (CA); Vasily Simanzhenkov, Calgary (CA); Xiaoliang Gao, Calgary (CA); David Sullivan, Calgary (CA); Marie Annette Barnes, Calgary (CA); Renee Laurel Anseeuw, Calgary (CA); Yipei Styles, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/846,942

(22) Filed: Apr. 13, 2020

(65) Prior Publication Data

US 2020/0238260 A1 Jul. 30, 2020

Related U.S. Application Data

(63) Continuation of application No. 16/041,064, filed on Jul. 20, 2018, now Pat. No. 10,661,256.

(30) Foreign Application Priority Data

Aug. 3, 2017 (CA) ..................................... 2975144

(51) Int. Cl.
*B01J 27/057* (2006.01)
*B01J 37/00* (2006.01)
(Continued)

(52) U.S. Cl.
CPC ............ *B01J 27/0576* (2013.01); *B01J 21/04* (2013.01); *B01J 21/063* (2013.01); *B01J 21/066* (2013.01);
(Continued)

(58) Field of Classification Search
CPC ...... B01J 27/0576; B01J 21/04; B01J 21/063; B01J 21/066; B01J 21/08; B01J 35/026;
(Continued)

(56) References Cited

U.S. PATENT DOCUMENTS 4,250,346 A * 2/1981 Young .................. C07C 51/215
502/209
4,524,236 A 6/1985 McCain
(Continued)

FOREIGN PATENT DOCUMENTS

CA 1262556 10/1989
EP 0 262 264 A1 4/1988
(Continued)

OTHER PUBLICATIONS

Balcells et al., "Partial oxidation of propane and propene to acrylic acid over a Mo—V—Te—Nb oxide catalyst," Catalysis Letters, dated Apr. 2003, 87(3-4):195-199.
(Continued)

*Primary Examiner* — Patricia L. Hailey
(74) *Attorney, Agent, or Firm* — Fish & Richardson P.C.

(57) ABSTRACT

Oxidative dehydrogenation catalysts for converting lower paraffins to alkenes such as ethane to ethylene when prepared as an agglomeration, for example extruded with supports chosen from slurries of $TiO_2$, $ZrO_2$ $Al_2O_3$, AlO (OH) and mixtures thereof have a lower temperature at which 25% conversion is obtained.

19 Claims, 5 Drawing Sheets

(51) Int. Cl.
| | |
|---|---|
| *B01J 37/10* | (2006.01) |
| *B01J 23/00* | (2006.01) |
| *C07C 11/04* | (2006.01) |
| *B01J 37/03* | (2006.01) |
| *B01J 37/06* | (2006.01) |
| *B01J 21/04* | (2006.01) |
| *B01J 21/06* | (2006.01) |
| *B01J 21/08* | (2006.01) |
| *B01J 35/02* | (2006.01) |
| *B01J 35/08* | (2006.01) |
| *B01J 35/10* | (2006.01) |
| *B01J 37/08* | (2006.01) |
| *C07C 5/48* | (2006.01) |

(52) U.S. Cl.
CPC ............ *B01J 21/08* (2013.01); *B01J 23/002* (2013.01); *B01J 35/026* (2013.01); *B01J 35/08* (2013.01); *B01J 35/1014* (2013.01); *B01J 35/1042* (2013.01); *B01J 35/1061* (2013.01); *B01J 37/0009* (2013.01); *B01J 37/0018* (2013.01); *B01J 37/0045* (2013.01); *B01J 37/03* (2013.01); *B01J 37/06* (2013.01); *B01J 37/082* (2013.01); *B01J 37/10* (2013.01); *C07C 5/48* (2013.01); *C07C 11/04* (2013.01); *B01J 2523/00* (2013.01); *B01J 2523/55* (2013.01); *B01J 2523/56* (2013.01); *B01J 2523/64* (2013.01); *B01J 2523/68* (2013.01); *C07C 2521/04* (2013.01); *C07C 2521/06* (2013.01); *C07C 2521/08* (2013.01); *C07C 2527/057* (2013.01)

(58) Field of Classification Search
CPC .... B01J 35/08; B01J 35/1014; B01J 35/1042; B01J 35/1061; B01J 37/0018; B01J 37/082; C07C 5/48; C07C 2521/04; C07C 2521/06; C07C 2521/08; C07C 2527/057
USPC .................................................. 502/311, 312
See application file for complete search history.

(56) References Cited

U.S. PATENT DOCUMENTS

| | | | |
|---|---|---|---|
| 6,841,699 B2* | 1/2005 | Bogan, Jr. ............. | B01J 23/002 502/311 |
| 7,319,179 B2 | 1/2008 | Lopez Nieto et al. | |
| 7,919,428 B2* | 4/2011 | Sutradhar ............. | B01J 23/002 502/215 |
| 8,846,996 B2 | 9/2014 | Kustov et al. | |
| 10,350,582 B2* | 7/2019 | Simanzhenkov ........ | B01J 35/02 |
| 10,661,256 B2* | 5/2020 | Kim ........................ | B01J 21/063 |
| 2010/0256432 A1* | 10/2010 | Arnold ...................... | C07C 5/48 585/655 |
| 2011/0245571 A1* | 10/2011 | Kustov ............... | B01J 27/0576 585/658 |
| 2012/0016171 A1* | 1/2012 | Kustov .................. | B01J 23/002 585/662 |
| 2014/0121433 A1 | 5/2014 | Cizeron et al. | |
| 2015/0119622 A1* | 4/2015 | De Rooij ............... | B01J 23/002 585/658 |
| 2015/0141727 A1 | 5/2015 | Simanzhenkov et al. | |
| 2017/0008821 A1 | 1/2017 | Hossain et al. | |
| 2019/0039050 A1* | 2/2019 | Gao ........................ | B01J 23/002 |

FOREIGN PATENT DOCUMENTS

| | | |
|---|---|---|
| EP | 18768941 A | 7/2018 |
| EP | 3661647 A1 | 6/2020 |
| JP | 2016539124 A | 12/2016 |
| RU | 2008143412 | 5/2010 |
| WO | WO2017029572 | 2/2017 |
| WO | WO2019025981 | 2/2019 |

OTHER PUBLICATIONS

Che-Galicia et al., "Modeling of oxidative dehydrogenation of ethane to ethylene on a MoVTeNbO/TiO2 catalyst in an industrial-scale packed bed catalytic reactor," Elsevier, Chemical Engineering Journal, dated Nov. 15, 2015, 280:682-694.
Japanese Office Action in Japanese Application No. 2020-505375, dated Feb. 2, 2021, 50 pages (with English translation).
Mishanin et al., "Advantages of ethane oxidative dehydrogenation on the MoVNbTeOx catalyst under elevated pressure," Elsevier, Mendeleev Communications, dated Feb. 13, 2019, 29(4):455-457.
Naraschewski et al., "Phase formation and selective oxidation of propane over MoVTeNbOx catalysts with varying compositions," Elsevier, Applied Catalysis A: General, dated Jan. 4, 2011, 391: 63-69.
P. Botella et al., "The influence of Te-precursor in Mo—V—Te—O and Mo—V—Te—Nb—O catalysts on their catalytic behaviour in the selective propane oxidation," Elsevier, Catalysis Today, dated Jan. 15, 2005, 99(1-2):51-57.
PCT International Preliminary Report on Patentability in International Application No. PCT/IB2018/055746, dated Feb. 13, 2020, 9 pages.
PCT International Search Report and Written Opinion in International Application No. PCT/IB2018/055746, dated Oct. 26, 2018, 11 pages.

* cited by examiner

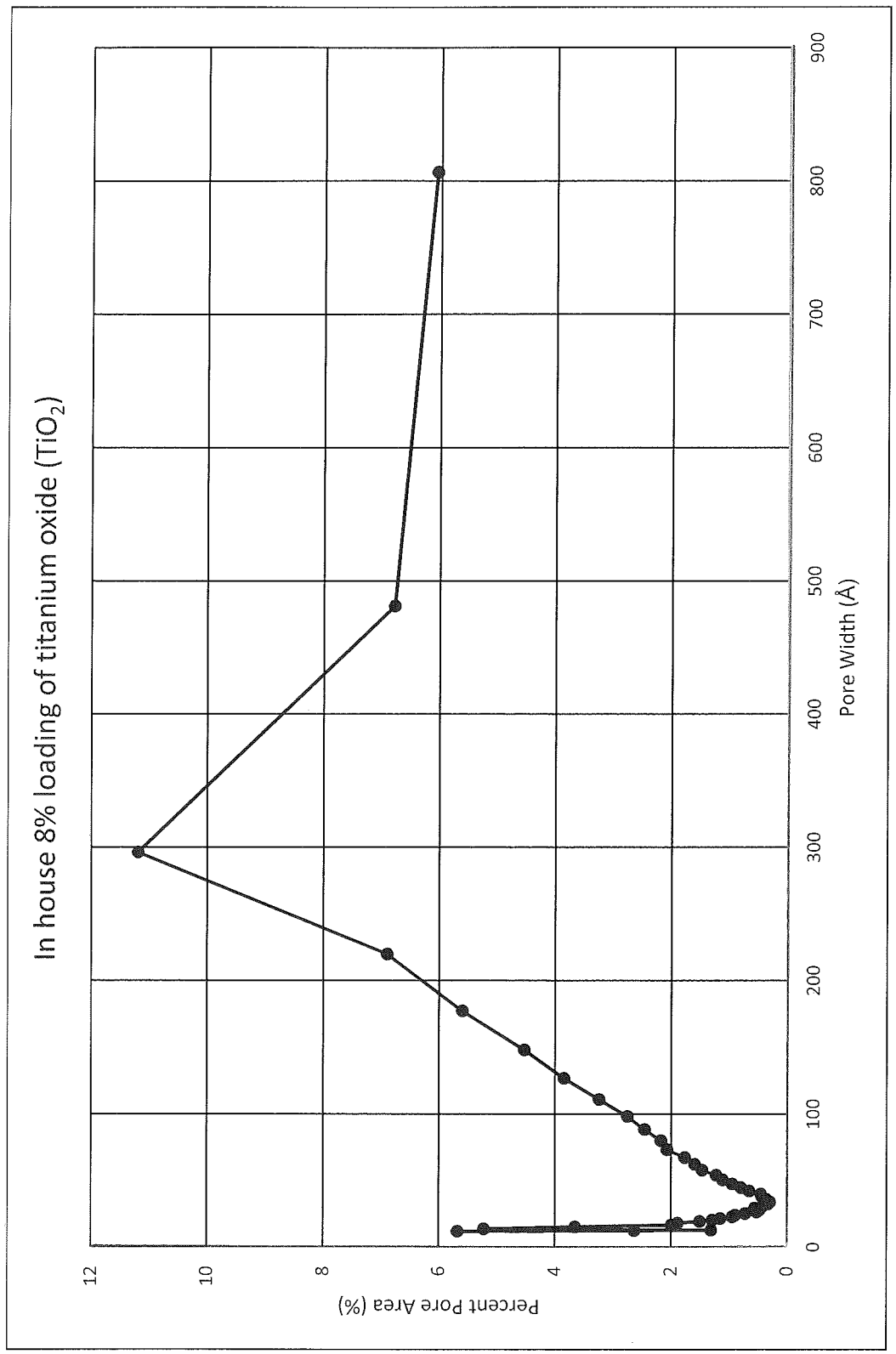
Figure 2: Activity at 25% conversion: 375°C - Selectivity at 25% conversion: 96%

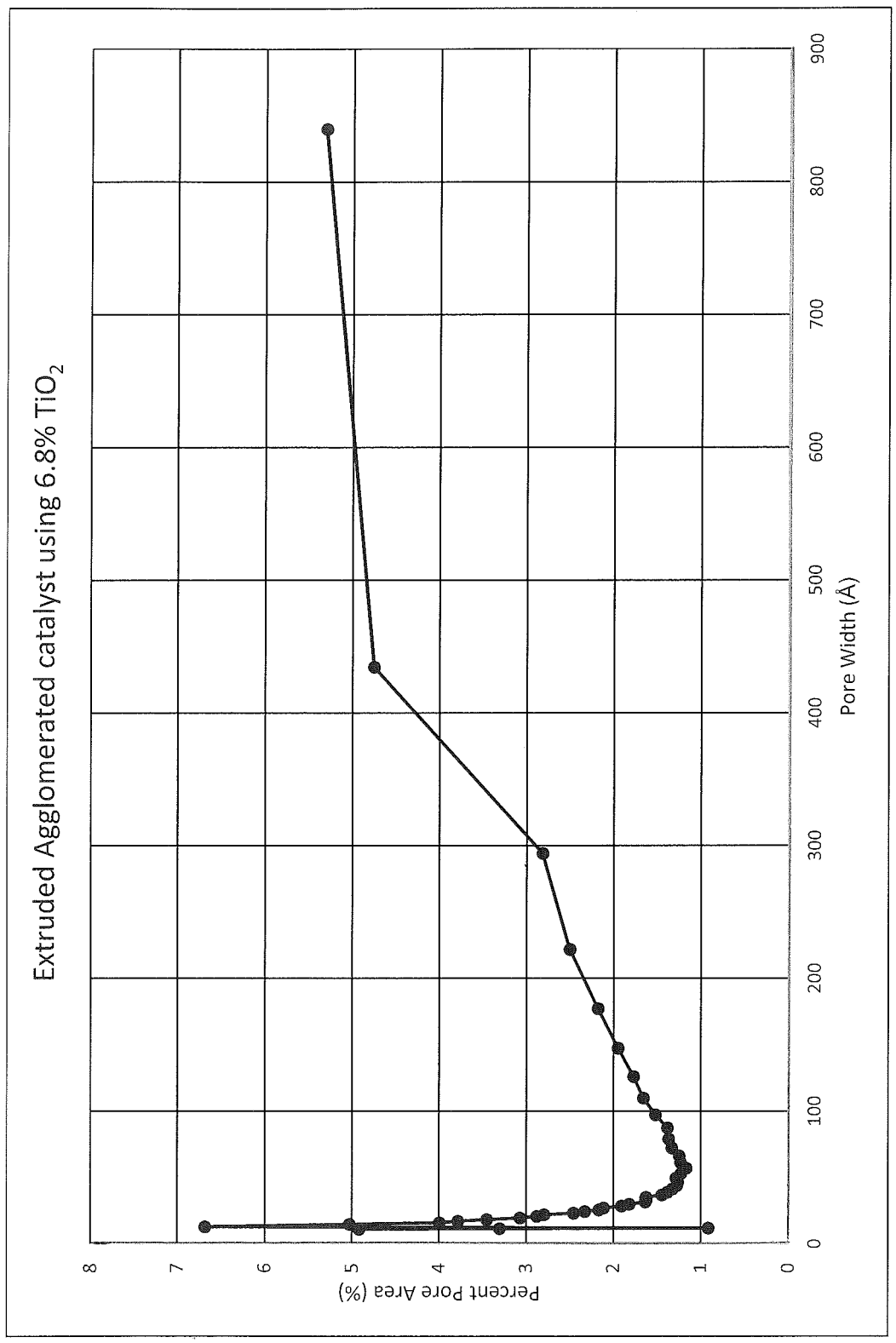
Figure 3: Activity at 25% conversion: 362°C - Selectivity at 25% conversion: 95%
Extruded Agglomerated catalyst using 6.8% $TiO_2$

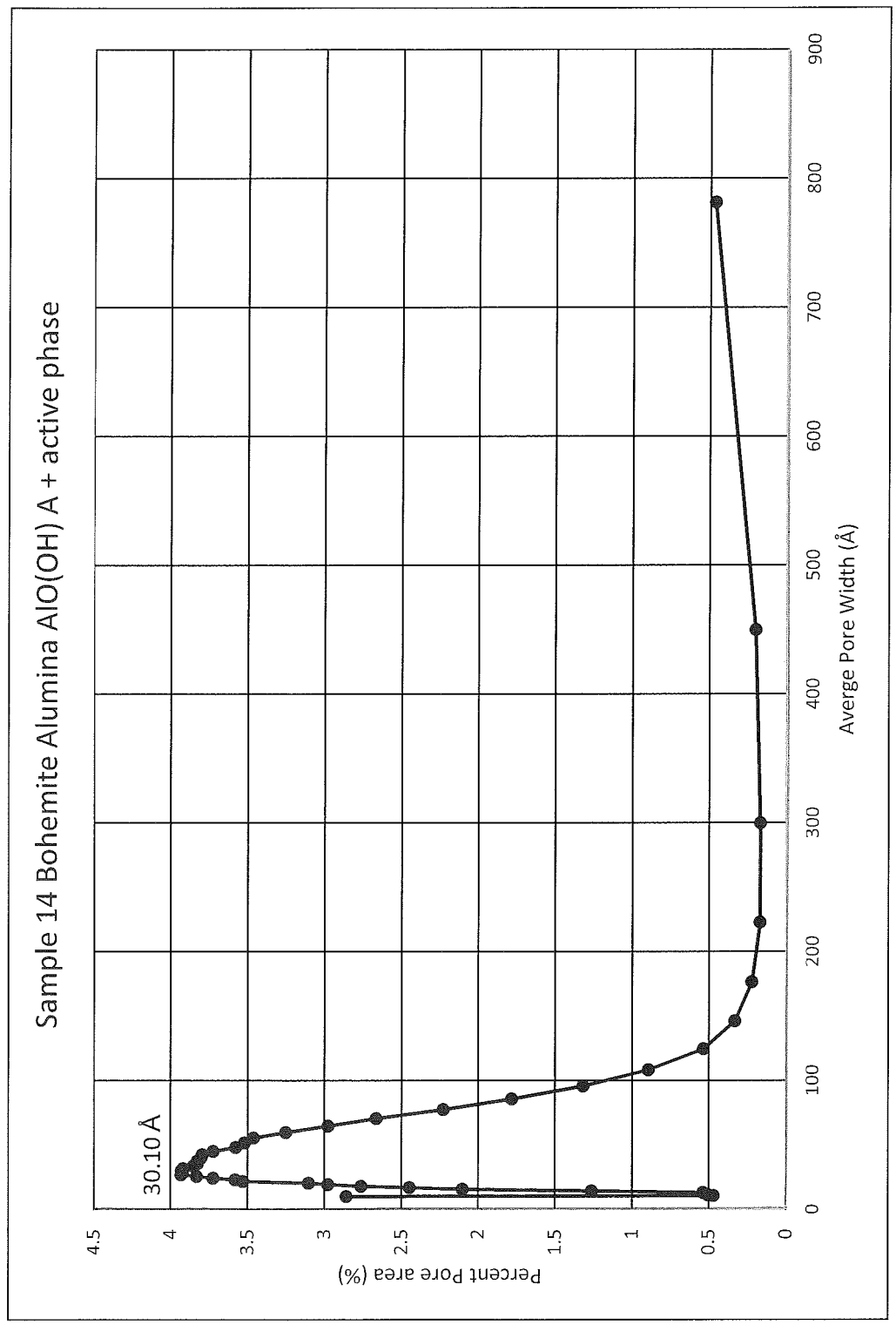

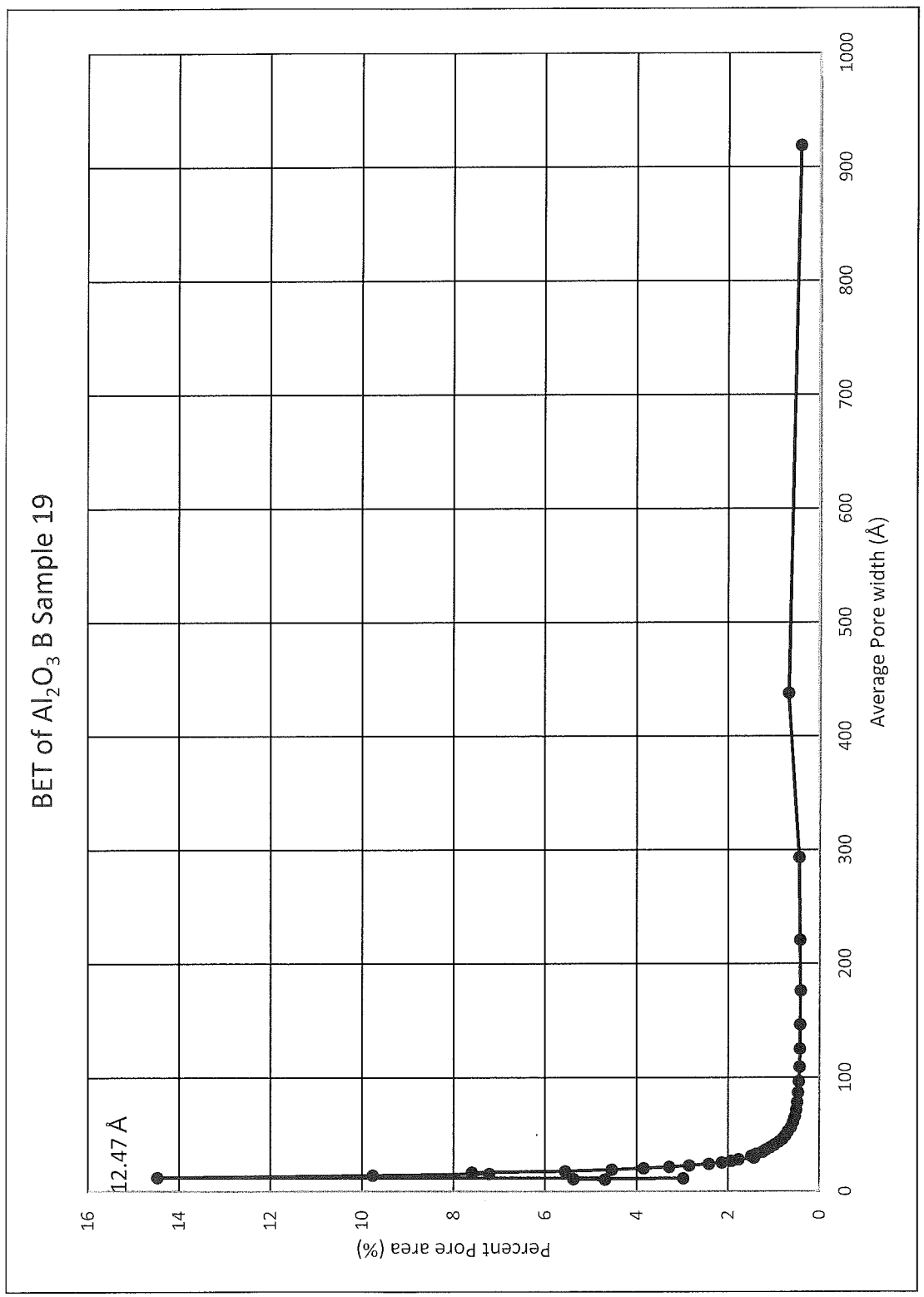
Figure 5: Activity at 25% conversion: 392°C - Selectivity at 25% conversion: 92%

AGGLOMERATED ODH CATALYST

CROSS REFERENCE TO RELATED APPLICATIONS

This application is a continuation application of U.S. application Ser. No. 16/041,064, filed on Jul. 20, 2018, which claims the benefit of the earlier filing date of Canadian application serial number 2975144 filed on Aug. 3, 2017, all of which are incorporated herein by reference in their entirety.

The present disclosure relates to agglomerated oxidative dehydrogenation catalysts to convert paraffins, for example $C_{2-4}$, or for example ethane, to the corresponding alkene. Such reactions may take place in fixed bed or fluidized bed reactors. There is a need to form catalyst particles having sufficient strength to avoid attrition during use. By selecting the appropriate binder for the catalyst particles the activity of the catalyst in terms of temperature at which 25% conversion is obtained may be improved without significant (e.g., less than 5%) reduction in selectivity.

U.S. Pat. No. 4,524,236 issued Jun. 18, 1985 to McCain assigned to Union Carbide Corporation teaches a catalyst for the oxidative dehydrogenation of ethane to ethylene comprising a calcined composition of $Mo_a\ V_b\ Nb_c\ Sb_d\ X_e$ wherein: x=at least one of the following: Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, and W; and
a=0.5 to 0.9
b=0.1 to 0.4
c=0.001 to 0.2
d=0.001 to 0.1.
e=0.001 to 1.0
The values of a, b, c, d and e constitute relative gram-atoms of the elements Mo, V, Nb, Sb, and X respectively, in the catalyst. The elements are present in combination with oxygen in a form of various oxides.

The patent teaches the catalyst may be used with or without a support. The catalyst is prepared as a solution and dried and calcined. The patent teaches Suitable supports for the catalyst include silica, aluminum oxide, silicon carbide, zirconia, titania, and mixtures thereof. When used on a support, the supported catalyst usually comprises from about 10 to 50% by weight of the catalyst composition, with the remainder being the support. The patent teaches the support is impregnated with the catalyst (Col. 4, lines 38 to 43).

European Patent Application 0 262 264 (corresponds to CA 1262556) published Mar. 30, 1988 in the name of Manyik et al., assigned to Union Carbide Corporation teaches a process to dehydrogenate ethane to ethylene using the catalyst of U.S. Pat. No. 4,524,236 issued Jun. 18, 1985 to McCain. The patent application teaches the catalyst solution is used to impregnate (i.e., an incipient wetness method) a support (page 7, lines 30-35). The supports have a surface area of less than about 1 square meter per gram and a relatively large median pore diameter of greater than 10 microns. The patent does not teach an agglomerated catalyst. The incipient wetness impregnations require the use of a solution of dissolved catalyst with a controlled type (improve adsorption into the pores) and volume of solvent to minimally wet the support. The pore size, the composition of the support (hydrophobic or hydrophilic) and type and amount of solvent place constraints on the up take and placement of active catalyst within the supported catalyst. An agglomeration method is conducted by blending dispersions of binder and support with optional reduction of solvent/diluent, extrusion and final drying. The agglomeration process gives a wider window for ratios of binder to catalyst and also provides enhanced control over pore volume, size and distribution.

U.S. Pat. No. 7,319,179 issued Jan. 15, 2008 to Lopez Nieto et al., assigned to Conseio Superior de Investigacionse Cientificas and Universidad Politecnica De Valencia teaches a five component metal oxide catalyst for the oxidative dehydrogenation of ethane. The patent teaches the catalyst can be a mixed oxide supported on a solid, such as, for example, silica, alumina, titanium oxide and mixtures thereof. In one embodiment, the silica, as solid support, is present in proportion of 20 to 70% by weight with respect to the total weight of catalyst. Moreover, the catalyst can also be in the form of a mixed oxide supported on a silicon carbide. The fixing of the different elements of the catalyst on the support can be done by conventional methods of impregnation, such as pore volume, excess solution, or simply by precipitation on the support of a solution containing the active elements. The patent seems to be teaching to individually bind each element of the catalyst on the support.

U.S. Published Application No. 20140121433 published May 1, 2014 in the name of Cizeron et al., assigned to Siluria teaches catalysts for oxidative coupling of methane. The disclosure seems to use the terms binder and diluent interchangeable. The oxidative coupling catalyst for methane (OCM) is a nanowire. The patent also teaches catalyst which may be used for oxidative dehydrogenation of ethane [357 and 358]. The passages at paragraphs [0146] through [0153] discuss "diluents". These appear to be inert. In any event the present disclosure does not contemplate nanowire composites.

U.S. Pat. No. 8,846,996 issued Sep. 30, 2014 in the name of Kustov et al., assigned to NOVA Chemicals (International) S.A. teaches co-comminution (wet or dry milling Col 5, line 50) of an oxidative dehydrogenation catalyst comparable to the present disclosure with an inert support selected from the group oxides of titanium, zirconium, aluminum, magnesium, yttrium, lanthanum, silicon and their mixed compositions or a carbon matrix, to produce particles having a size from 1 to 100 microns and forming the resulting particles into pellets having a size from 0.1 to 2 mm. The present disclosure has done away with the co-comminution step. Additionally the product of the co-comminution step is formed into pellets and crushed to obtain the right particle size (Col. 5, line 55).

U.S. Published Application No. 20170008821 published Jan. 12, 2017 in the name of Hossain et al., assigned to King Fahd University of Petroleum and Minerals teaches an oxidative dehydrogenation process conducted in the absence of gaseous oxygen conducted in a circulating stirred bed reactor. The catalyst comprises lattice oxygen. When the oxygen is depleted from the catalyst, it is circulated to an oxidation reactor where the lattice oxygen is replenished. The catalyst is supported on an alumina based support which has been treated with $ZrO_2$ using an incipient wetness process (paragraph 64). The catalyst is then supported on the treated support also using an incipient wetness process. The catalyst is not prepared using an extrusion method.

The present disclosure seeks to provide an (extruded) agglomerated catalyst for the oxidative dehydrogenation of ethane which may be extruded into various shapes having improved activity. The catalysts are extruded onto acid supports chosen from: $TiO_2$, $ZrO_2$, $Al_2O_3$, AlO(OH) and mixtures thereof, provided that $ZrO_2$ is not used together with an aluminum containing binder.

Provided herein is an agglomerated, for example extruded, catalyst comprising:
from 10 to 95, or for example from 25 to 80, or for example from 30 to 45, weight % of a catalyst of the formula: $Mo_{1.0}V_{0.12-0.49}Te_{0.6-0.16}Nb_{0.15-0.20}O_d$ wherein d is a number to satisfy the valence of the oxide; and from 5-90, for example from 20 to 75, or for example from 55 to 70 weight % of a binder chosen from acidic, basic or neutral binder slurries of $TiO_2$, $ZrO_2$ $Al_2O_3$, AlO(OH) and mixtures thereof provided that $ZrO_2$ is not used in combination with an aluminum containing binder.

In a further embodiment, the agglomerated catalyst has a cumulative surface area less than 35 $m^2/g$ as measured by BET, alternatively, less than 20 $m^2/g$, alternatively, less than 3 $m^2/g$.

In a further embodiment, the agglomerated catalyst has a cumulative pore volume from 0.05 to 0.50 cm3/g.

In a further embodiment, the agglomerated catalyst has a pore size distribution so that less than 4% of the pores have a pore width size less than 150 Angstroms.

In a further embodiment, the agglomerated catalyst has a percent pore area distribution less than 40% and corresponding percentage of pore volume less than 20%.

In a further embodiment, the agglomerated catalyst is in the shape of a sphere, rod, ring, or a saddle having a size from about 1.3 mm to 5 mm.

In a further embodiment, the binder is an acidified binder.

In a further embodiment, the binder is a base treated binder.

In a further embodiment, the binder is chosen from $TiO_2$, $Al_2O_3$, $ZrO_2$, AlO(OH) and mixtures thereof provided $ZrO_2$ is not mixed with an aluminum based binder.

In a further embodiment, the agglomerated catalyst is in the shape of rods having an aspect ratio from 1 to 5/1.3 having a crush strength up to 100 N/mm.

In a further embodiment, the agglomerated catalyst is in the shape of spheres having a crush strength up to 100 N.

In a further embodiment, in the agglomerated catalyst the catalyst has the empirical formula:

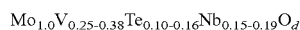

$Mo_{1.0}V_{0.25-0.38}Te_{0.10-0.16}Nb_{0.15-0.19}O_d$ where d is a number to satisfy the valence of the oxide.

In a further embodiment, in the agglomerated catalyst the catalyst has the empirical formula $Mo_{1.0}V_{0.22-033}Te_{0.10-0.16}Nb_{0.15-0.19}O_d$ as determined by PIXE where d is a number to satisfy the valence of the oxide.

In a further embodiment, in the agglomerated catalyst the catalyst has the empirical formula as measured by PIXE: $Mo_{1.0}V_{0.12-0.19}Te_{0.14-0.16}Nb_{0.15-0.19}O_d$ where d is a number to satisfy the valence of the oxide.

In a further embodiment in the agglomerated catalyst, the catalyst has the empirical formula as measured by PIXE: $Mo_{1.0}V_{0.17-0.20}Te_{0.06-0.07}Nb_{0.19-0.20}O_d$ where d is a number to satisfy the valence of the oxide.

In a further embodiment in the agglomerated catalyst, the catalyst has the empirical formula as measured by PIXE: $Mo_{1.0}V_{0.12-0.19}Te_{0.14-0.16}Nb_{0.15}O_d$ where d is a number to satisfy the valence of the oxide.

In a further embodiment, there is provided a method to prepare a catalyst as above comprising:
  i) forming an aqueous slurry or paste of catalyst comprising 10 to 95 wt. % of catalyst;
  ii) adding to the slurry or paste up to 5 to 90 wt % on of a binder chosen from $TiO_2$, $ZrO_2$ and $Al_2O_3$, AlO(OH) and mixtures thereof provided that $ZrO_2$ is not used in combination with an aluminum based binder, in the form of an acidic, neutral or basic colloidal suspension having a pH up to12, for exmaple from 1 to 12;
  iii) where required reducing the water content of the resulting slurry or paste to less than 30 wt %;
  iv) extruding the water reduced slurry or paste to form a, rod, ring or a saddle having a size from about 1.3 mm to 5 mm:
  v) drying the particles in an oxygen containing atmosphere at a temperature from 90° C. up to 115° C.; and
  vi) calcining the resulting particles at a temperature of up to 600° C.

In a further embodiment in step vi), the particles are calcined at a temperature of less than 350° C.

In a further embodiment, the rod shaped agglomerated particles are spheroidized at a temperature up to 300° C. and then further calcining the resulting spheres at temperatures up to 600° C.

The present disclosure further provides a method for the oxidative dehydrogenation of a mixture comprising oxygen and one or more $C_{2-4}$ alkanes comprising passing the mixture over an extruded agglomerated catalyst as described herein, at a temperature from 340° C. to less than 420° C., a pressure from 172.3 kPag (25 psig) up to 689 kPag (100 psig), a space velocity from 500 $hr^{-1}$ to 3000 $hr^{-1}$, and a residence time from 0.002 to 20 seconds.

In a further embodiment, the oxidative dehydrogenation process comprising increasing the amount of binder in the extruded catalyst within the range of binder in the catalyst in the range from 5 to 50 wt % and increasing the gas flow rate through the catalyst bed by a proportional amount while maintaining the bed temperature less than 420° C., for example less than 395° C., or for example less than 385° C. and maintaining the selectivity within ±3%.

BRIEF DESCRIPTION OF THE DRAWINGS

FIG. 2 is a plot of the percentage pore area of a catalyst with $TiO_2$ binder as function of pore width (sample 5) measured by BET (pore width distribution by percent pore area).

FIG. 3 is a plot of the percentage pore area of an extruded catalyst with $TiO_2$ binder as function of pore width (sample 25) measured by BET.

FIG. 4 is a plot of the percentage pore area of a catalyst, which was not extruded having a 60% AlO(OH) binder as function of pore width (sample 14) measured by BET (pore width distribution by percent pore area).

FIG. 5 is a plot of the percentage pore area of a catalyst, which was not extruded having a 60% $Al_2O_3$ binder as function of pore width (sample 19 measured by BET (pore width distribution by percent pore area).

NUMBERS RANGES

Figure 1:
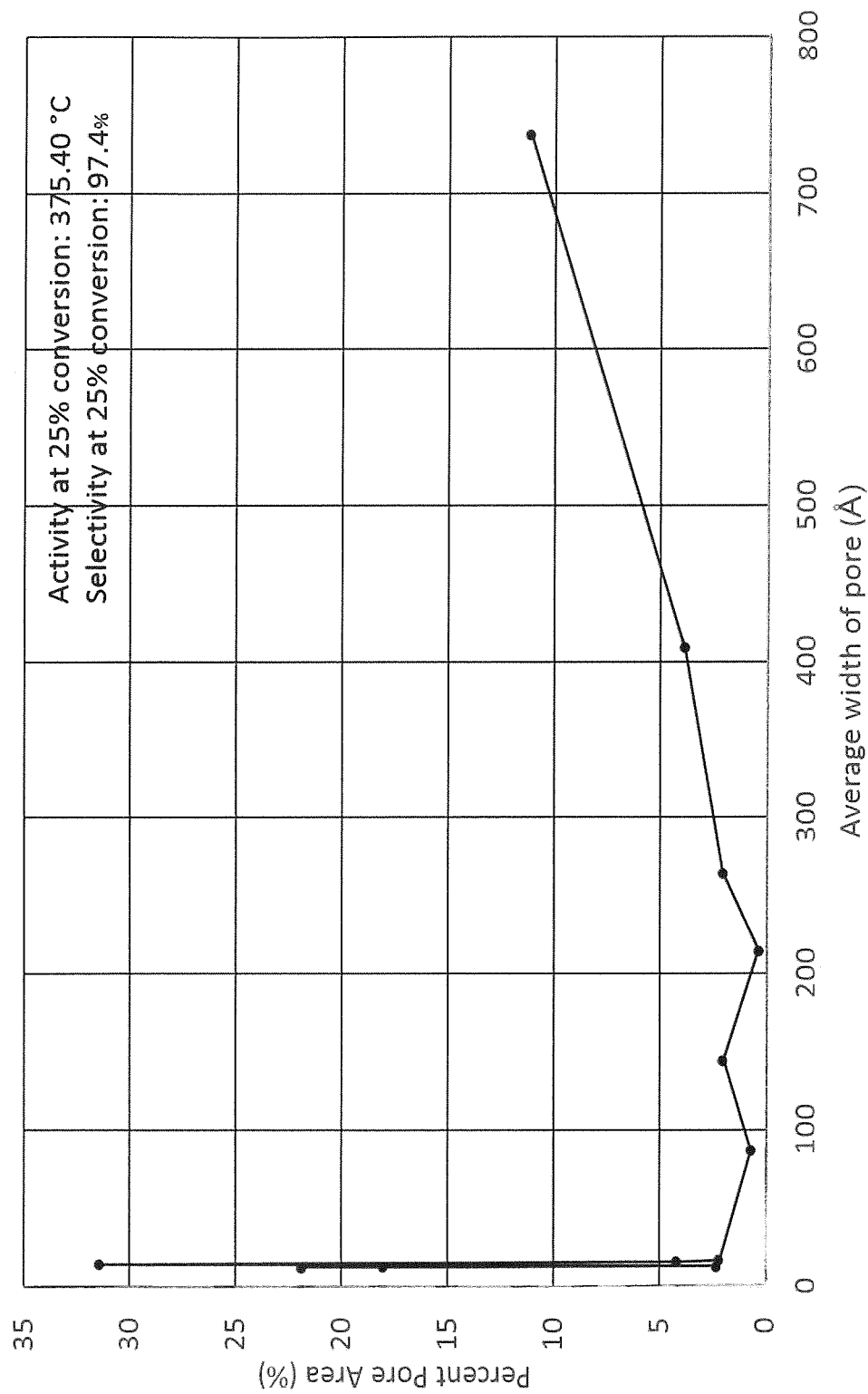
FIG. 1. is a plot of the percentage pore area of a catalyst with no binder as function of pore width (sample 13) measured by BET (pore width distribution by percent pore area).

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components actually used will conform to the maximum of 100 percent.

Binder means a material added to the catalyst t to increase cohesion among the catalyst particles and optionally to improve adhesion of the catalyst to the support if present.

In the specification, the phrase "the temperature at which there is 25% conversion of ethane to ethylene" is determined by plotting a graph of conversion to ethylene against temperature typically with data points below and above 25% conversion or the data is fit to an equation and the temperature at which there is a 25% conversion of ethane to ethylene is determined. In some instances in the examples the data had to be extrapolated to determine the temperature at which 25% conversion occurred.

In the specification, the phrase "selectivity at 25% conversion" is determined by plotting the selectivity as function of temperature or fit to an equation. Then having calculated the temperature at which 25% conversion occurs one can determine either from the graph or from the equation the selectivity at that temperature.

There are a number of ways to relate the surface area to the volume of gas, which can be incorporated into the agglomerated support.

One methods is cumulative pore volume ($cm^3/g$) and cumulative surface area ($m^2/g$).

A second method is distribution of pore width to percentage of surface area (for example, what surface area of the catalyst has a pore size of a defined diameter) In FIG. 4, 4% of the pore area has a range of pore width (diameter) of 5-150 A. The remaining 96% of the pore area has a pore width (diameter) greater than 150 A.

The third method comprises:
first determining the cumulative surface area as function of cumulative pore volume;
secondly, normalize the cumulative surface area and cumulative pore volume to create percentages of the total distribution; and thirdly, plotting the surface area percentage as a function of pore volume percentage.

For the oxidative dehydrogenation of lower ($C_{2-4}$) alkanes such as ethane, the molecules being treated and the product molecules have a diameter from about 2.5-4 Angstroms (0.25-0.40 nm). The molecule diameter, the pore diameter and pore surface area influences the probability of the molecule interacting with a catalyst (on the pore wall or surface). For example large diameter pores, low inner surface area, and large pore volume would have the lowest probability of molecules making contact with the material inner surface (catalyst) resulting in a lower conversion.

One family of catalysts useful in the oxidative dehydrogenation of lower alkanes such as $C_{2-4}$ alkanes and, for example ethane, to $C_{2-4}$ alkenes and, for example ethylene, are catalysts of mixed oxides of molybdenum, vanadium, tellurium, niobium and optionally other components such as Pt, Pd, Ta, Ti, W, Hf, Zr, Sb Zn, Sc, Y, La, Ce, Ta, Cr, W, U, Te, Fe, Co and Ni) for the oxidative dehydrogenation of ethane to ethylene.

One family of catalysts useful for the oxidative dehydrogenation of alkanes, and for example lower $C_{2-4}$ alkanes had the formula:

$Mo_{1.0}V_{0.12-0.38}Te_{0.6-0.16}Nb_{0.11-0.20}O_d$ wherein d is a number to satisfy the valence of the oxide.

The composition of the catalyst may vary within the above generic formula depending on how the catalyst is manufactured.

In some embodiments, such catalysts and precursors therefore are made using a hydrothermal process.

In some embodiments, in the hydrothermal process, the precursor is prepared by:
i) forming an aqueous solution of ammonium heptamolybdate (tetrahydrate) and telluric acid at a temperature from 30° C. to 85° C. and adjusting the pH of the solution to from 6.5 to 8.5, for example from 7 to 8, or for example from 7.3 to 7.7 with a nitrogen containing base to form soluble salts of the metals;
ii) preparing an aqueous solution of vanadyl sulphate at a temperature from room temperature to 80° C. (or for example 50° C. to 70° C., or for example 55° C. to 65° C.);
iii) mixing the solutions from steps i) and ii) together;
iv) slowly (dropwise) adding a solution of niobium monoxide oxalate ($NbO(C_2O_4H)_3$) to the solution of step iii) to form a slurry; and
v) heating the resulting slurry in an autoclave under an inert atmosphere at a temperature from 150° C. to 190° C. for not less than 6 hours.

The resulting solid from step v) is filtered and washed with deionized water, and drying the washed solid for a time from 4 to 10 hours at a temperature from 70 to 100° C.

In a further embodiment, the precursor is calcined in an inert atmosphere at a temperature from 200° C. to 600° C. for a time from 1 to 20 hours.

The above is a typical hydrothermal process to prepare a precursor and final oxidative dehydrogenation catalyst.

If the catalyst is made using a conventional hydrothermal process, it may have the formula:

$Mo_{1.0}V_{0.25-0.45}Te_{0.10-0.16}Nb_{0.15-0.19}O_d$ where d is a number to satisfy the valence of the oxide.

In some preparation methods, the dried catalyst precursor is treated with a peroxide, typically hydrogen peroxide. The hydrogen peroxide treatment may take place at atmospheric pressure and room temperature (e.g., from 15° C. to 30° C.) to about 80° C., in some instances from 35° C. to 75° C. in other instances from 40° C. to 65° C. The hydrogen peroxide may have a concentration from 10 to 30 wt. %, in some instances from 15 to 25 wt. % in water. The treatment time may range from 1 to 10 hours, in some cases from 2 to 8 hours, in other cases from 4 to 6 hours. The catalyst precursor is treated with the equivalent of from 0.3-2.8, in some embodiments from 0.3-2.5 ml of a 30 wt. % solution of aqueous $H_2O_2$ per gram of precursor. The treatment should be in a slurry (e.g. the precursor is at least partially suspended) to provide an even distribution of $H_2O_2$ and to control the temperature rise. For post calcination treatment with $H_2O_2$ there is a sudden delayed violent reaction with $H_2O_2$. This results in an instantaneous reaction which is more controlled and safer.

The treated catalyst precursor is then subject to calcining to produce the active oxidative dehydrogenation catalyst. The treated precursor may be calcined in an inert atmosphere at a temperature from 200° C. to 600° C. for a time from 1 to hours. The purge gases used for calcining are inert gases, including one or more of nitrogen, helium, argon, $CO_2$ (for example high purity >90%), said gases or mixture containing less than 1 vol.-% hydrogen or air, at 200-600° C., for example at 300-500° C. The calcining step may take from 1 to 20, in some instances from 5 to 15 in other instances from about 8 to 12 hours, or for example about 10 hours. The resulting mixed oxide catalyst is a friable solid typically insoluble in water. In some embodiments, the calcined product has a bulk density from 1.20 to 1.90 g/cc. This bulk density is based on how much 1.5 ml of pressed and crushed catalyst weighs.

When the peroxide treatment is used, the catalyst may have the formula:

$$Mo_{1.0}V_{0.22-0.33}Te_{0.10-0.16}Nb_{0.15-0.19}O_d$$ as determined by PIXE where d is a number to satisfy the valence of the oxide.

In some processes, the hydrothermal treatment may be carried out at a controlled low pressure from 10 psi to 190 psi (960 kPa to 1300 kPa). This may be achieved by having a vent to the autoclave and some suitable pressure control means such as a regulator or in some instances a column of a liquid, such as water, through which the vent gasses escape. In such a process the duration of the hydrothermal treatment may extend up to 72 hours.

When prepared by this method the catalyst may have the formula:

$$Mo_{1.0}V_{0.32-0.49}Te_{0.10-0.17}Nb_{0.14-0.17}O_d$$

where d is a number to satisfy the valence of the oxide.

In some methods, the pressure in the hydrothermal reactor may be reduced even further to a range from 1 to 8 psig (6.89 kPag to 55.1 kPag), for example less than 5 psig (34.4 kPag) above atmospheric pressure. Under these conditions the catalyst may have the empirical formula as measured by PIXE:

$$Mo_{1.0}V_{0.12-0.19}Te_{0.14-0.16}Nb_{0.15}O_d$$

where d is a number to satisfy the valence of the oxide

The present disclosure contemplates the use of mixtures or combinations of the above materials.

In accordance with the present disclosure from 10 to 95 weight %, for example from 25 to 80 weight %, or for example from 30 to 45 weight % of the catalyst is agglomerated (extruded) with from 5 to 90 weight %, for example from 20 to 75 weight %, or for example from 55 to 70 weight % of one or more binders chosen from acidic, $TiO_2$, $ZrO_2$, $Al_2O_3$, AlO(OH) and mixtures thereof provided that $ZrO_2$ is not mixed with an aluminum compound.

The agglomerated catalyst may be prepared by methods known to those skilled in the art. In one embodiment the calcined catalyst is suspended in a diluent, typically water and prepared or purchased acidic, neutral or basic suspensions of binder(s) are added to the catalyst suspension in the amounts noted above.

The binder may be chosen from, $TiO_2$, $ZrO_2$, $Al_2O_3$, and AlO(OH) and mixtures thereof. In some embodiments $ZrO_2$ is not mixed with an aluminum based binder.

The binder may be purchased or made as an acidic, neutral or basic paste slurry or suspension containing from about 3 wt % to 90 wt %, in some embodiments 20 wt % to 80 wt % of the binder, typically from about 40 to 60 wt % of the binder. The balance of the binder is a volatile diluent, typically water. Other additives can be present in the binder solution for improving binder adhesion to active phase. The paste, slurry or suspension of the binder may have a pH from about 0.5 to 12, in some embodiments 3 to 6. The paste, slurry or suspension of the binder may be acidified using a conventional acid chosen from hydrochloric acid, hydrobromic acid, hydroiodic acid, per chloric acid, sulfuric, nitric acid, and organic acids and mixtures thereof. The basic paste, slurry or suspension of the binder may be treated with common bases, for example volatile bases such as lower di $C_{1-6}$ alkyl amines with a pH from 7.5 to 12, in some embodiments from 8 to 10.

The slurry of binder is added to the slurry of catalyst to form a paste, slurry or slip (herein after referred to as slip). The slip is prepared without the co-comminution of the catalyst and the binder. The diluent is partially separated from the suspension typically by drying but other means such as filtering or applying a vacuum may be suitable. The content of diluent (water) in the resulting slip is generally reduced to less than 30 wt %, or for example less than 25 wt %, in some embodiments less 20 wt %. In some embodiments, the blend is heated at temperatures from about 90 to 100° C. at atmospheric pressure. As noted above, in some instances a vacuum may be applied resulting a corresponding reduction in temperature to remove the diluent. It is important that the partially dried mixtures is sufficient fluid that it may flow through the extruder under normal operating conditions.

To improve the flow properties of the mixture or slip, it may be desired to include one or more flow improving agents and/or extrusion aids in the mixture prior to extrusion. Suitable additives for inclusion in the mixture include cellulose or its derivatives, fatty amines, quaternary ammonium compounds, polyvinyl pyridine, polyvinyl alcohol, sulphoxonium, sulphonium, phosphonium and iodonium compounds, alkylated aromatic compounds, acyclic monocarboxylic acids, fatty acids, sulphonated aromatic compounds, alcohol sulphates, ether alcohol sulphates, sulphated fats and oils, phosphonic acid salts, polyoxyethylene alkylphenols, polyoxyethylene alcohols, polyoxyethylene alkylamines, polyoxyethylene alkylamides, polyacrylamides, polyols and acetylenic glycols. Some additives are sold under the trademarks Nalco and Superfloc.

The compaction pressure in the extruder was adjusted to produce structures with average (side) crush strengths up to 100 N (22.5 lb).

The resulting product (slip) has the consistency of a paste or a thick paste (e.g. mud). The paste is extruded, passing through a cutter into a shaped product such a sphere, rod, including trilobite rods, ring or a saddle and then dried. The particles, for example rods, may be subject to spheritization to produce spheres having a diameter up to about 5 mm, or for example from about 2 to 3 mm.

Growth Agglomeration (Agitation Methods)

Extruded particles may be aggregated with each other in a fluid flowing system. This is usually done in the presence of liquid and binders. The particle size enlargement occurs by coalescence or aggregation (snowballing) based on capillary forces. In a few exceptional cases, the major cohesive force is the van der Waals force. Usually the agglomerates are spherical with diameters between 0.5 and 20 mm. Typical equipment types include drums, cones, pans, paddle mixers and plowshare mixers.

The extruded/aggregated product may have a diameter from about 0.5 to 5 mm, or for example from 1.3 to 2.5 mm, or for example from 1.35 to 1.45 mm and a length of up to 8 mm, or for example less than 5 mm. The particles may have an aspect ratio from 1 (e.g. a sphere) to 5/1.3.

As the slip passes through the extruder a number of changes occur. The extruder may help to reduce the content of the diluent (e.g. water) in the product. Depending on the pressure in the extruder it will collapse some of the interstitial voids within the slip. As a result the extruded and dried particles may have a surface area less than 35 m$^2$/g, alternatively, less than 20 m$^2$/g, alternatively, less than 3.0 m$^2$/g as measured by BET. At high loadings of binder greater than 20 wt % the surface area of the agglomerated catalyst may increase in some embodiments at high loadings of the binder (e.g. 60 wt %) the surface area may go as high as about 250 m$^2$/g.

As a result, the agglomerated and dried particles may have a pore volume range from about 0.05 to 0.50 cm3/g. The resulting shaped product is then dried in air at a temperature from about 80° C. to about 150° C., typically less than 120° C., in some embodiments less than 110° C. The dried particulate catalyst is then calcined at a temperature from 300° C. to 600° C., in some embodiments from 350° C., to 500° C. The agglomerated catalyst is calcined for a period of time of not less than 1 hour, typically up to about 4 hours.

The final particle should have a crush strength sufficiently to withstand the operating condition in the ODH reactor. The crush strength may range up to 100 N/mm, in some embodiments 10 N/mm (2.25 lb) or less (e.g. for rods). The resulting agglomerated catalyst may have a pore size distribution less than 4% having pore width size less than 150 Angstroms. Alternatively, resulting agglomerated catalyst may have a cumulative pore volume from 0.05 to 0.50 cm3/g.

Oxidative Dehydroaenation Reaction

In some embodiments, the oxidative dehydrogenation (ODH) process comprises passing a mixed feed of ethane and oxygen at a temperature less than 420° C. in some instances less than 410° C., in some instances less than 400° C., in some instances less than 390° C., in some instances less than 380° C. The catalysts discosed herein may be used at temperatures, at a gas hourly space velocity of not less than or for example not less than 1500 hr$^{-1}$, for example at least 3000 hr$^{-1}$ through one or more fixed beds at a pressure from 0.8 to 1.2 atmospheres. In some embodiments the catalyst permits the oxidative dehydrogenation reactor operates at temperatures, for example from 300° C. to 450° C., in some instances from 330 to 380° C. in some embodiments from 340° C. to 360° C. at a space velocity from 500 hr$^{-1}$ to 3000 hr$^{-1}$.

The outlet pressure from the ODH reactor may be from 105 kPag (15 psig) to 172.3 kPag (25 psig) and the inlet pressure is higher by the pressure drop across the bed which depends on a number of factors including reactor configuration, particle size in the bed and the space velocity. In some embodiments the pressure drop may be below 689 kPag (100 psig) or for example less than 206.7 kPag (30 psig).

The residence time of one or more alkanes, typically C$_{2-4}$ alkanes, in the reactor is from 0.002 to 20 seconds.

The feed to the oxidative dehydrogenation reactor includes oxygen in an amount above the upper explosive/flammability limit. For example for ethane oxidative dehydrogenation, in a feed stream comprising oxygen and ethane, in some embodiments the oxygen will be present in an amount of not less than about 16 mole % for example about 18 mole %, for example from about 22 to 27 mole %, or 23 to 26 mole %. It is desirable not to have too great an excess of oxygen as this may reduce selectivity arising from combustion of feed or final products. Additionally, too high an excess of oxygen in the feed stream may require additional separation steps at the downstream end of the reaction. In some circumstances the feed stream may be diluted with a feed gas having a low reactivity such as nitrogen, argon, helium $CO_2$, CO, steam.

In some embodiments, the percentage of alkane may be up to 40 mole %. For instances where the mixture of gases prior to ODH comprises 25 mole % oxygen and 40 mole % alkane, the balance may be made up with an inert diluent, such as nitrogen, carbon dioxide, or steam. The inert diluent should exist in the gaseous state in the conditions within the reactor and should not increase the flammability of the hydrocarbon added to the reactor, characteristics that a skilled worker would understand when deciding on which inert diluent to employ.

The goal is for 100% conversion, of alkane with minimal unreacted alkane and oxygen leaving the ODH reactor, and a minimum production of carbon monoxide or carbon dioxide. In some embodiments, the product stream leaving the ODH reactor contains less than 5% unreacted lower alkane, for example less than 2.5%, or for example less than 1%. In another embodiment, the product stream leaving the ODH reactor contains less than 2% oxygen, for example less than 1.5% oxygen, of for example less than 1% oxygen.

In a further embodiment, in the oxidative dehydrogenation process, the amount of binder in the extruded catalyst is increased within range from 5 to 50 wt % and the gas flow rate through the catalyst bed is increased by a proportional amount (e.g., the amount of binder is increased by 10% the gas flow rate is increased by up to 10%) while maintaining the bed temperature less than 420° C., for example less than 395° C., or for example less than 285° C., and maintaining the selectivity within ±3%.

This improves the economics of the reaction akin to increasing the productivity.

The present invention will now be illustrated by the following non limiting examples.

Example 1

A base catalyst was prepared using a conventional hydrothermal process as described above. The calcined catalyst had the empirical formula:

$$Mo_{1.0}V_{0.25-0.45}Te_{0.10-0.16}Nb_{0.15-0.19}O_d$$

where d is a number to satisfy the valence of the oxide.

The catalyst was dispersed in water and mixed with various binders both basic, acidic and neutral. The compositions are listed in Table 1 below.

TABLE 1

| Binder Component | Concentration (wt % in H2O) | Specific Gravity | Surface Area (m²/g) | pH | Notes |
|---|---|---|---|---|---|
| TiO2 | 19.4 | Not given | 342 | 1.3 | Wt. % 3-5 HNO3, 0.58 SO3, and 0.14 P2O5 mg/kg: 35 Fe |
| TiO2 | 18.0 | Not given | 311 | 12 | Wt. % 2-5 diethylamine, 0.54 SO3, and 0.16 P2O5 mg/kg: 40 Fe |
| SiO2 | 30 | 1.210-1.250 | 230 | 4.5 | Acidic Cl counter ion. |
| SiO2 | 30 | 1.197-1.215 | 230 | 9.1 | Basic NH4, counter ion |
| SiO2 | 30 | 1.202-1.219 | 220 | 9.8 | Basic Na counter ion |
| Al2O3 | 20 | 1.19 | Not given | 4.0 | Acidic 0.5% nitric acid |
| ZrO2 | 20 | 1.24 | Not given | 4.0 | Acidic 0.3 mol/mol nitric acid |
| SiO2 | 140 | | | 4-7 | Deionized no counter ion |
| AlO(OH) | N/A | Not given | 320 | N/A | |
| AlO(OH) | N/A | Not given | 250 | N/A | |
| Al2O3 | N/A | Not given | Not given | N/A | |

The amount of binder (weight %) based on elemental weight percentage composition of the solution is indicated in the table. The resulting slurry was extruded or spheritized as above, dried 90-100° C. and re-calcined in air at 350-500° C. The agglomerated particles were tested in a lab scale dehydrogenation reactor. Where ethane and oxygen in about a 1:1 molar ratio were passed through a fixed bed at the same rate of flow of the starting feedstock. The temperature at which 25% conversion occurred and the selectivity at that conversion were recorded. The results are set forth in tables 2, 3 and 4.

TABLE 2

| Sample # | Catalyst Code | Temperature at 25% Conversion (° C.) | Selectivity at 25% Conversion (%) |
|---|---|---|---|
| Sample 1 | Baseline Catalyst | 367 | 98 |
| Sample 2 | Active Phase + 4% acidic TiO2 binder + HNO3 | 356 | 97 |
| Sample 3 | Active Phase + 1M HNO3 | 366 | 97 |
| Sample 4 | Active Phase + 4% acidic TiO2 binder | 357 | 97 |
| Sample 5 | Active Phase + 8% acidic TiO2 binder | 357 | 96 |
| Sample 6 | Active Phase + 8% basic TiO2 binder | 357 | 97 |
| Sample 7 | Active Phase + 8% Al2O3 A binder | 361 | 98 |
| Sample 8 | Active Phase + 8% deionized, neutral SiO2 binder | 372 | 97 |
| Sample 9 | Active Phase + 40% acidic TiO2 binder | 350 | 87 |
| Sample 10 | Active Phase + 8% acidic SiO2 binder | 385 | 97 |
| Sample 11 | Active Phase + 8% basic SiO2 binder | 374 | 97 |
| Sample 12 | Active Phase + 8% neutral ZrO2 binder | 361 | 97 |
| Sample 25 | Extruded catalyst with 6.8% TiO2 binder | 362 | 95 |

TABLE 3

ODH active phase catalyst mixed with 60% wt of either AlO(OH) or Al2O3 calcined at 350° C.

| Sample # | Catalyst Code | Temperature at 25% Conversion (° C.) | Selectivity at 25% Conversion (%) |
|---|---|---|---|
| Sample 13 | Active phase baseline (catalyst baseline) | 375 | 97 |
| Sample 14 | Active phase + 60% AlO(OH) A binder | 356 | 96 |
| Sample 15 | Active phase + 60% acidic AlO(OH) A binder | 361 | 96 |
| Sample 16 | Active phase + 60% AlO(OH) B binder | 357 | 95 |
| Sample 17 | Active phase + 60% AlO(OH) C binder | 371 | 93 |
| Sample 18 | Active phase + 60% AlO(OH) B binder | 365 | 91 |
| Sample 19 | Active phase + Al2O3 B binder | 392 | 92 |
| Sample 20 | Active phase + 70% AlO(OH) A binder | 368 | 96 |
| Sample 21 | Active phase + 70% AlO(OH) B binder | 360 | 96 |

TABLE 4

ODH active phase catalyst mixed with 60% wt of either AlO(OH) or Al2O3 calcined at 500° C.

| Sample # | Catalyst Code | Temperature at 25% Conversion (° C.) | Selectivity at 25% Conversion (%) |
|---|---|---|---|
| Sample 22 | Active phase + 60% AlO(OH) A binder | 362 | 90 |
| Sample 23 | Active phase + 60% AlO(OH) B binder | 363 | 90 |
| Sample 24 | Active phase + 60% AlO(OH) A binder calcined at 350° C. and then at 500° C. | 370 | 88 |

The results support the following conclusions.

1. SiO2 is an antagonist to the catalyst for the oxidative dehydrogenation of ethylene (Samples 8, 10, and 11). The temperature at which there is 25% conversion of ethane to ethylene goes up.

2. The addition of only an acid to the catalyst has virtually no effect (Samples 1 and 3).

3. The use of 4 to 8 wt % of TiO2 as a binder whether acidic or basic reduces the temperature at which 25% conversion is achieved by about 10° C. (Samples 1, 4, 5, and 6).

4. The use of 40 wt % of acidic TiO2 as a binder reduces the temperatures at which 25% conversion occurs by about 16° C. (Samples 1 and 9).

5. The use of 8 wt % of a binder of $ZrO_2$ reduces the temperature at which 25% conversion occurs by about 6° C. (Samples 1 and 12).
6. The use of 8 wt % of a binder of $Al_2O_3$ reduces the temperature at which 25% conversion occurs by about 6° C. (Samples 1 and 8).
7. The use of 60% AlO(OH) reduces the temperature at which 25% conversion occurs by about 20° C. (Samples 14-16 and 18).
8. The use of 70% AlO(OH) reduces the temperature at which 25% conversion occurs by about 15° C. (Samples 20 and 21).
9 Calcination of a catalyst comprising 60 wt. % of AlO(OH) at 350° C. to form the agglomerated catalyst mixture has a selectivity of 6% higher than calcination at 500° C. to form the agglomerated catalyst mixture (Samples 22 and 23).

Example 2

Samples 3, and 10, were retested under different conditions in the lab scale dehydrogenation reactor. The flow rate for the feed in standard cubic centimeters per minute (SCCM) was increased proportionately relative to the proportion of binder used in the base case—no binder. In other words, the whole of the agglomerated particles mass (binder plus active phase) were tested as catalyst.

TABLE 5

| Catalyst | Feed gas flow (sscm) | Temperature at 25% Conversion (° C.) | Selectivity to ethylene (%) |
| --- | --- | --- | --- |
| Baseline ODH Catalyst (I) | 140 (no compensation) | 367 | 98 |
| (I) + 40% $TiO_2$ (Sample 10) | a) 140 | 350 | 87 |
|  | b) 196 (40% increase) | 366 | 90 |
| (I) + 8% $SiO_2$ A | a) 140 | 385 | 97 |
|  | b) 151 (8% increase) | 390 | 98 |
| (I) + 8% SiO B | a) 140 | 374 | 97 |
|  | b) 151 (8% increase) | 380 | 97 |
| (I) + 8% $ZrO_2$ | a) 140 | 361 | 97 |
|  | b) 151 (8% increase) | 368 | 97 |

The examples show that by increasing the amount of binder with a corresponding increase in the gas feed rate there is a rise in the reaction temperature but still below 380° C. and the selectivity is maintained or increased.

What is claimed is:

1. An agglomerated catalyst comprising:
   10 wt. % to 95 wt. % of a catalyst of the formula:

$Mo_{1.0}V_{0.12-0.49}Te_{0.06-0.16}Nb_{0.15-0.20}O_d$ as measured by PUCE and wherein d is a number to satisfy the valence of the oxide; and
   5 wt. % to 90 wt. % of a binder chosen from $TiO_2$, $Al_2O_3$, AlO(OH), and mixtures thereof,
   wherein the agglomerated catalyst comprises aggregated extrudate particles; and
   wherein the agglomerated catalyst comprises a cumulative pore volume from 0.05 to 0.50 cm$^3$/g.

2. The agglomerated catalyst of claim 1, having a cumulative surface area of less than 35 m$^2$/g as measured by BET.

3. The agglomerated catalyst of claim 1, having a pore size distribution with less than 4% having a pore width size less than 150 Angstroms.

4. The agglomerated catalyst of claim 1, wherein the agglomerated catalyst is in the shape of a sphere, rod, ring, or a saddle.

5. The agglomerated catalyst of claim 4, wherein the agglomerated catalyst has an average size from 1.3 mm to 5 mm.

6. The agglomerated catalyst of claim 4, wherein the binder is an acidified binder.

7. The agglomerated catalyst of claim 6, wherein the agglomerated catalyst is in the shape of a rod having an aspect ratio from 1 to 5/1.3 and a crush strength up to 100 N/mm.

8. The agglomerated catalyst of claim 6, wherein the agglomerated catalyst is in the shape of a sphere having a crush strength up to 100 N.

9. The agglomerated catalyst of claim 4, wherein the binder is a base treated binder.

10. The agglomerated catalyst of claim 9, wherein the agglomerated catalyst is in the shape of a rod having an aspect ratio from 1 to 5/1.3 and a crush strength up to 100 N/mm.

11. The agglomerated catalyst of claim 9, wherein the agglomerated catalyst is in the shape of a sphere having a crush strength up to 100 N.

12. The agglomerated catalyst of claim 4, wherein the catalyst has the empirical formula:

$Mo_{1.0}V_{0.25-0.38}Te_{0.10-0.16}Nb_{0.15-0.19}O_d$ as measured by PIXE and wherein d is a number to satisfy the valence of the oxide.

13. The agglomerated catalyst of claim 4, wherein the catalyst has the empirical formula:

$Mo_{1.0}V_{0.22-0.33}Te_{0.10-0.16}Nb_{0.15-0.19}O_d$ as measured by PIXE and wherein d is a number to satisfy the valence of the oxide.

14. The agglomerated catalyst of claim 4, having the formula:

$Mo_{1.0}V_{0.12-0.19}Te_{0.14-0.16}Nb_{0.15}O_d$ as measured by PIXE and wherein d is a number to satisfy the valence of the oxide.

15. A method to prepare the catalyst of claim 1, the method comprising:
   providing an aqueous slurry or paste comprising the catalyst;
   providing to the aqueous slurry or paste the binder chosen from $TiO_2$, $Al_2O_3$, AlO(OH), or a mixture thereof, in the form of an acidic, neutral, or basic colloidal suspension having a pH up to 12 to provide a mixture comprising a precalcined catalyst;
   extruding the mixture comprising the precalcined catalyst to form precalcined catalyst particles chosen from a rod, a ring, a saddle, or a combination thereof and having a size from 1.3 mm to 5 mm;
   drying the precalcined catalyst particles in an oxygen containing atmosphere to provide dried precalcined catalyst particles; and
   aggregating the precalcined catalyst particles in a fluid flowing system to form agglomerated catalyst particles;
   calcining the agglomerated catalyst particles at a temperature of up to 600° C. to provide the agglomerated catalyst of claim 1, wherein the agglomerated catalyst comprises a cumulative pore volume from 0.05 to 0.50 cm$^3$/g.

16. The method of claim 15, further comprising reducing the water content of the mixture comprising the precalcined catalyst to less than 30 wt. % prior to extruding the mixture comprising the precalcined catalyst to form precalcined catalyst particles.

17. The method of claim 15, wherein the agglomerated catalyst particles are calcined at a temperature of less than 350° C.

18. The method of claim 15, wherein the mixture comprising the precalcined catalyst is extruded to form precalcined catalyst particles comprising rods and the method further comprises spheroidizing the rod shaped precalcined catalyst particles at a temperature up to 300° C. to provide sphere shaped precalcined catalyst particles.

19. A method for the oxidative dehydrogenation of a mixture comprising oxygen and one or more $C_{2-4}$ alkanes comprising passing the mixture over the agglomerated catalyst of claim 1, at a temperature from 340° C. to 420° C., a pressure from 172.3 kPag (25 psig) up to 689 kPag (100 psig), a space velocity from 500 $hr^{-1}$ to 3,000 $hr^{-1}$, and a residence time from 0.002 to 20 seconds.

* * * * *